United States Patent [19]

Tong et al.

[11] Patent Number: 5,087,738

[45] Date of Patent: Feb. 11, 1992

[54] MULTIFUNCTIONAL CYCLOBUTARENE PEROXIDE POLYMERIZATION INITIATORS

[75] Inventors: Wen H. Tong, Midland, Mich.; Duane B. Priddy, Terneuzen, Netherlands

[73] Assignee: The Dow Chemical Company, Midland, Mich.

[21] Appl. No.: 703,951

[22] Filed: May 22, 1991

Related U.S. Application Data

[62] Division of Ser. No. 530,382, May 30, 1990, Pat. No. 5,034,485.

[51] Int. Cl.$^5$ .................. C07C 409/38; C07C 409/32; C07C 409/16
[52] U.S. Cl. .................................... 560/302; 568/558; 568/561; 568/563; 568/566
[58] Field of Search ................ 560/302; 568/558, 561, 568/563, 566

[56] References Cited

U.S. PATENT DOCUMENTS

| | | | |
|---|---|---|---|
| 4,469,862 | 10/1984 | Komai | 528/271 |
| 4,540,763 | 9/1985 | Kirchoff | 526/281 |
| 4,698,394 | 10/1987 | Wong | 525/289 |

*Primary Examiner*—Joseph L. Schofer
*Assistant Examiner*—M. Nagumo
*Attorney, Agent, or Firm*—Charles J. Enright

[57] ABSTRACT

Multifunctional cyclobutarene peroxide polymerization initiators comprising at least one cyclobutarene moiety linked through the aromatic ring to at least one peroxide containing group which catalyze free radical polymerizations, as well as participate in cyclobutarene initiated ring opening polymerizations. The cyclobutarene peroxides of this invention are useful for the production of cross-linked, branched and graft polymeric compositions.

8 Claims, No Drawings

MULTIFUNCTIONAL CYCLOBUTARENE PEROXIDE POLYMERIZATION INITIATORS

CROSS-REFERENCE TO RELATED APPLICATION

This is a division of application Ser. No. 530,382, filed May 30, 1990, now U.S. Pat. No. 5,034,485.

FIELD OF THE INVENTION

This invention relates to novel polymerization initiators, and more particularly to multifunctional polymerization initiators which can catalyze free radical polymerizations, as well as participate in thermally initiated ring opening polymerization reactions.

BACKGROUND OF THE INVENTION

It has long been known to use various peroxides as initiators for the free radical catalytic polymerization of low molecular weight materials to form polymers. These polymerizations are performed with a wide variety of starting materials to form many useful polymers that have numerous desirable properties which depend upon the nature of the starting material, the degree of polymerization, the extent of branching and the extent of crosslinking.

More recently it has been discovered that various cyclobutarene containing materials can be induced to undergo polymerization by subjecting these materials to elevated temperatures. Since these reactions consume the cyclobutarene moiety, useful materials often are biscyclobutarenes in which two cyclobutarene moieties are connected by various bridging or linking groups or structures. Low molecular weight materials containing two cyclobutarene moieties can polymerize linearly through ring opening polymerization reactions of the two cyclobutarene moieties.

If an average of more than two polymerizable functionalities are included per unit of starting material, branching and crosslinking reactions are possible. These reaction types are also attainable through the use of multiple polymerization mechanisms.

A process is disclosed in U.S. Pat. No. 4,708,990 wherein a living polymer of the alkenyl type is end-capped with an arylcyclobutene monomer end-capping agent. Secondary polymerization of the polymer can then be induced by heating. Cyclobutarene moieties have been incorporated in polymers through reactions involving cyclobutarene monomers containing alkylenic unsaturation, as, for example, in U.S. Pat. No. 4,698,394.

It is highly desirable to have a multifunctional monomeric material which can be used as an initiator to catalyze free radical polymerizations wherein the material fragments of the initiator are incorporated in the polymer, and which fragments can subsequently be induced to participate in other polymerizations or reactions. It would be particularly desirable to be able to differentiate and control the extent of the various reactions by means of some easily controllable reaction parameter such as temperature.

SUMMARY OF THE INVENTION

The present invention relates to novel cyclobutarene peroxides comprising at least one cyclobutarene moiety linked through the aromatic ring to at least one peroxide containing group where the cyclobutarene peroxide is represented by the formula:

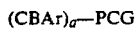

where CBAr is a cyclobutarene moiety, PCG is a peroxide containing group and a is an integer of at least 1. The peroxide containing group PCG may contain more than one peroxide—OO—moiety, and it may be linked to one or more cyclobutarene moieties.

In another embodiment the present invention is a polymeric composition produced by the reaction of a polymerizable material, such as a monoalkenyl arene monomer, in a free radical polymerization reaction which is initiated by a cyclobutarene peroxide, wherein the cyclobutarene fragments are incorporated into the polymer. A polymeric product can be produced from the polymeric composition of the free radical polymerization by ring opening polymerization of the cyclobutarene moiety to produce branched, crosslinked or a mixture of branched and crosslinked polymers.

In a further embodiment the present invention provides a process for the production of branched and crosslinked polymers by conducting a first polymerization of a free radical polymerizable material, such as a monoalkenyl arene monomer, in a free radical polymerization reaction which is initiated by a cyclobutarene peroxide, wherein the cyclobutarene fragments are incorporated into the polymer, followed by a secondary polymerization comprising ring opening polymerization of the cyclobutarene moiety to produce branched, crosslinked or a mixture of branched and crosslinked polymers.

The cyclobutarene peroxides of this invention are useful as multifunctional polymerization initiators which can initiate free radical polymerization reactions wherein cyclobutarene containing fragments are incorporated into the polymer. Further reactions can then be carried out by subjecting the initial reaction product to reaction conditions which result in a secondary polymerization reaction which involves the cyclobutarene moiety. The polymers of the present invention have characteristics which make the useful for a wide variety of end uses such as fabrication of molded articles. The processes of the present invention are useful for the production of these polymers.

Preferred Embodiments

For the purposes of describing this invention, a cyclobutarene is a substituted or unsubstituted aromatic compound to which is fused one or more cyclobutane rings or one or more substituted cyclobutane rings. The aromatic rings of the cyclobutarene can be substituted with nitro, chloro, bromo, or any other group that does not adversely affect either the initiation of free radical polymerizations by the cyclobutarene peroxide, or the ring opening polymerization reaction of the incorporated cyclobutarene moieties. Techniques for the synthesis of cyclobutarene monomers and other cyclobutarene containing materials useful in the present invention are disclosed in U.S. Pat. Nos. 4,540,763, 4,642,329, 4,724,260, 4,730,030, 4,812,588 and 4,831,172 which are hereby incorporated by reference. Any of these cyclobutarene monomers and cyclobutarene containing materials can be used as a cyclobutarene moiety of the instant invention when bonded to a peroxide containing group through a cyclobutarene aromatic ring.

Acid chloride derivatives of cyclobutarenes are known and may be prepared by the methods disclosed in U.S. Pat. No. 4,540,763, which has been incorporated herein by reference.

The cyclobutarene peroxides of the present invention can be prepared by reacting an acid chloride derivative of a cyclobutarene with a peroxide under basic conditions. In general, the acid chloride derivative of the cyclobutarene, either neat or in solution, and a solution of concentrated aqueous base such as sodium hydroxide, are slowly added to a stirred aqueous solution which is 2-20% in peroxide, typically hydrogen peroxide. The peroxide solution should be cold at the start and a temperature of about 0° C. for the reaction mixture is maintained throughout, conveniently with an ice bath. The period of addition may be a few minutes to a few hours, with the rate adjusted so that the temperature does not rise significantly. The product is isolated and purified by solvent extraction of the organic phase with a solvent such as methylene chloride, followed by neutralization, filtration and crystallization.

One aspect of the present invention is novel cyclobutarene peroxides comprising at least one cyclobutarene moiety linked through the aromatic ring to at least one peroxide containing group where the cyclobutarene peroxide is represented by the formula:

(CBAr)$_a$—PCG where CBAr is a cyclobutarene moiety, PCG is a peroxide containing group and a is an integer of at least 1. In preferred embodiments the peroxide moiety—OO—is bonded to a carbonyl carbon or a tertiary carbon of an alkyl or alkylene.

In one embodiment where a of the general formula above is equal to 1 and the peroxide containing group PCG is —R—OO—R$^1$, cyclobutarene peroxides of the present invention can be represented by the formula:

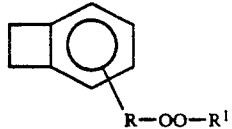

where R is carbonyl, C$_{2-10}$ acylene or C$_{1-10}$ alkylene and R$^1$ is C$_{2-10}$ acyl or C$_{1-10}$ alkyl. In preferred embodiments the peroxide moiety—OO—is bonded to a carbonyl carbon or a tertiary carbon. Examples of cyclobutarene peroxides of this form are represented by any one of the formulae:

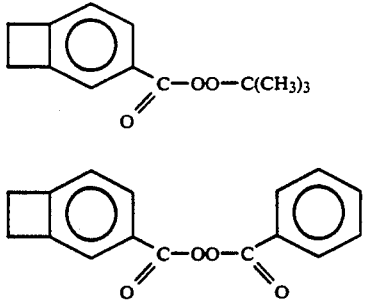

In another embodiment, which is especially preferred, where a of the general formula is 2, PCG of the cyclobutarene peroxide is linked to two cyclobutarene moieties. These cyclobutarene peroxides can be represented by the formula:

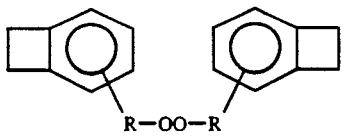

where R is as previously defined.

Examples of this form of cyclobutarene peroxide is represented by any one of the formulae:

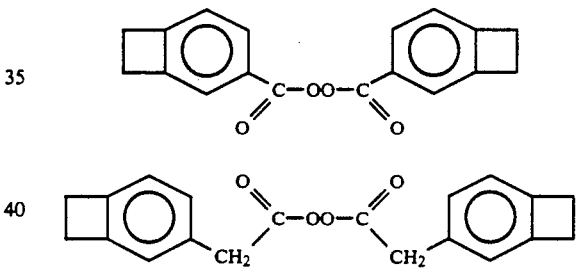

In another embodiment PCG of the cyclobutarene peroxide can be represented by the formula:

CBAr—R—OO(—R—R$^2$—R—OO—)$_n$—X where R and R$^1$ are as previously defined, R$^2$ is hydrocarbylene of 1 to about 20 carbons, n is an integer equal to 1 to 5 and X is R$^1$ or —R—ArCB. A preferred embodiment is for X to be —R—ArCB. An example of this type of cyclobutarene peroxide is represented by any one of the formulae:

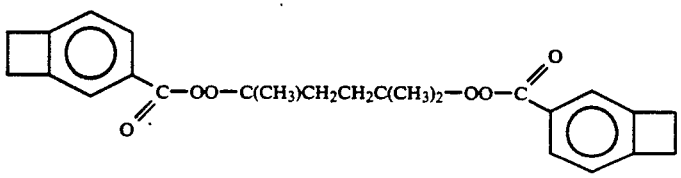

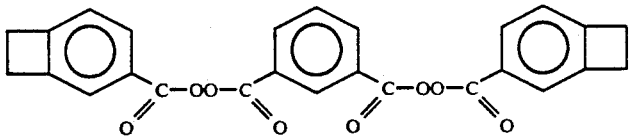

Within the scope of the present invention are polymeric compositions produced by the reaction of a free radical polymerizable material in a free radical polymerization reaction which is initiated by a cyclobutarene peroxide, wherein the cyclobutarene fragments are incorporated into the polymer. Preferred free radical polymerizable materials include monoalkenyl arene monomers, conjugated diene monomers, acrylic or methacrylic acid and their derivatives, or a mixture of any two or more of these monomers. Suitable monoalkenyl arene monomers for use in this invention are styrene and the alkyl and halo derivatives thereof. Suitable conjugated diene monomers for use in this invention are 1,3-butadiene, isoprene and the alkyl and halo derivatives thereof. Any of the cyclobutarene peroxides described and discussed above are suitable for the production of these polymeric compositions.

Also within the scope of the present invention are polymeric products produced by the ring opening polymerization reaction of the polymeric composition produced by the polymerization reaction of a free radical polymerizable material, such as a monoalkenyl arene monomer, a conjugated diene monomer, acrylic or methacrylic acid or a derivative thereof, or a mixture of any two or more of these monomers in a free radical polymerization reaction which is initiated by a cyclobutarene peroxide, wherein the cyclobutarene fragments are incorporated into the polymer. Suitable monomers for use in this embodiment of the present invention have been discussed above. Any of the cyclobutarene peroxides described and discussed above are suitable for the production of these polymeric products.

Further embodiments of the present invention are processes for the production of the polymeric compositions and the polymeric products discussed above. The ranges of process conditions for the production of these compositions and products are well known in the art. In general, the free radical polymerization may be accomplished with a concentration of cyclobutarene peroxide which is from about 0.01% to about 2% in weight relative to the weight of polymerizable material. Reaction temperatures are typically in the range of about 50° C. to about 150° C., with a typical preferred range of from about 70° C. to about 120° C. The reaction may be run neat, with the polymerizable material serving as a solvent for the cyclobutarene peroxide initiator, or, as is often preferred, with a solvent. Typical solvents useful in the process are aromatic compounds and substituted aromatics, such as ethylbenzene. The amount of solvent may range from zero to about 100% of the weight of the polymerizable material, with 5-20% being a preferred range. Naturally, in any production process it is desirable to keep the amount of solvent which must be recycled to an absolute minimum.

Conversion of the polymeric compositions which are the reaction products of the free radical polymerization process into other polymeric products is accomplished by ring opening reactions of the cyclobutarene moieties which have been incorporated into the the polymeric compositions during the initiation phase of the free radical reaction. Ring opening reactions of cyclobutarenes are often described as being analogous to the reactions of various dienes, and, thus, cyclobutarenes typically react with dienophiles. Ring opening is usually thermally initiated, so the conversion reaction is accomplished simply by heating the reaction mixture containing the polymerizable composition to a sufficiently high temperature that the reaction proceeds at a convenient rate, preferably to about 220° C. or less.

The polymers produced by the processes of this invention, the polymeric compositions and the polymeric products have a wide variety of uses as films and sheets, as molded and shaped articles, and in the form of various foamed materials with useful properties such as insulation.

The polymers produced by a first polymerization through a free radical reaction will contain cyclobutarene moieties on one or both ends of the polymer molecules. This can be controlled to some degree by the choice of reaction conditions. When these singly and doubly cyclobutarene end-terminated polymers are subjected to reaction conditions suitable for ring opening polymerization through the cyclobutarene moieties, the singly end-terminated polymers will react to form essentially branched polymeric compositions, while those polymers which are doubly end-terminated will form crosslinked polymeric compositions. This is shown in the following Reaction Scheme I.

REACTION SCHEME I

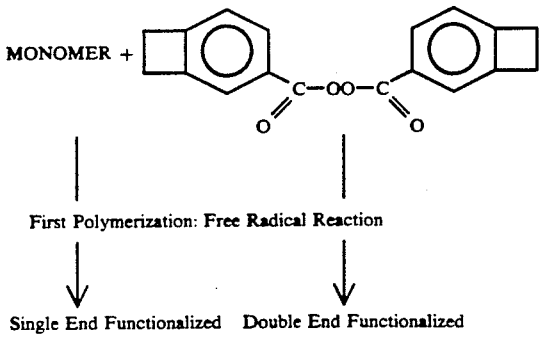

-continued
REACTION SCHEME I

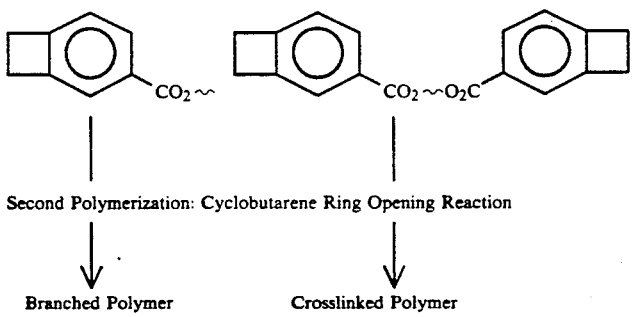

End functionalized polymers which are singly end-terminated with a cyclobutarene moiety can be mixed with other polymers containing unsaturation to form graft copolymers. This permits the compatibilization of a cyclobutarene end functionalized polymer with many other polymers. This is as shown in the following Reaction Scheme II.

REACTION SCHEME II

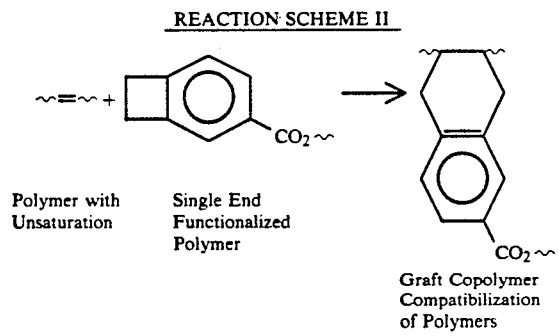

Polymer with Unsaturation  Single End Functionalized Polymer

Graft Copolymer Compatibilization of Polymers

The following examples are intended to be illustrative only and do not in any way limit the scope of the invention.

EXAMPLE 1

In a 2 oz glass jar with a magnetic stirrer was placed 2 g of 30 percent $H_2O_2$ and 10 ml of deionized water. The contents of the jar were kept at 0° C. with an ice bath. Slowly 1 g of

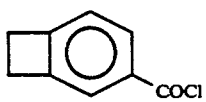

and 1.5 ml of 5N NaOH were added alternately in a dropwise fashion. A white solid precipitated during the reaction. After the reagents had been added, the mixture was stirred for another hour at 0° C. The reaction mixture was then extracted with methylene chloride. The organic solution was washed twice with 1N NaOH followed by deionized water. The organic phase was dried by allowing it to stand overnight over anhydrous $MgSO_4$. The solution was clarified by filtration and then evaporated to yield a white crystalline solid. The diacyl peroxide structure of the product bis-benzocyclobutenyl diacyl peroxide was confirmed by infrared spectroscopy.

EXAMPLE 2

Polymerization of Styrene using Bis-benzocyclobutenyl Diacyl Peroxide

A solution of 5 g styrene and 0.025 g of bisbenzocyclobutenyl diacyl peroxide was placed in a Pyrex glass tube 3 inches long and 0.5 inch in diameter. The glass tube was capped with a rubber cap and the rubber capped glass tube was put into a metal sleeve with a screw cap to protect it. The tube was submerged into a 90° C. silicon oil bath for 5 hours. The conversion was 96.2 percent by measuring percent solids after the polymerization. The similar polymerization without the peroxide gave 4.8 percent conversion.

What is claimed is:

1. A cyclobutarene peroxide comprising at least one cyclobutarene moiety linked through the aromatic ring to at least one peroxide containing group, the cyclobutarene peroxide being represented by the formula:

$(CBAr)_a$—PCG where CBAr is a cyclobutarene moiety, PCG is a peroxide containing group and a is an integer of at least 1.

2. The cyclobutarene peroxide of claim 1 wherein a is 1, and the peroxide containing group PCG is —R—OO—R$^1$ and the cyclobutarene peroxide is represented by the formula:

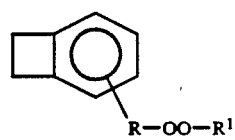

where R is carbonyl, $C_{2-10}$ acylene or $C_{1-10}$ alkylene and R$^1$ is $C_{2-10}$ acyl or $C_{1-10}$ alkyl.

3. The cyclobutarene peroxide of claim 2 wherein the cyclobutarene peroxide is represented by any one of the formulae:

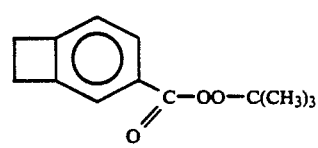

-continued

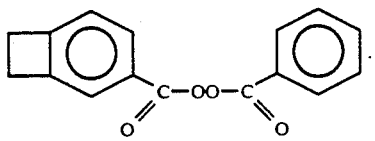

4. The cyclobutarene peroxide of claim 1 wherein a is 2 and the cyclobutarene peroxide is represented by the formula:

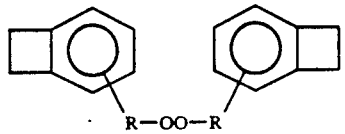

where R is as previously defined.

5. The cyclobutarene peroxide of claim 4 represented by any one of the formulae:

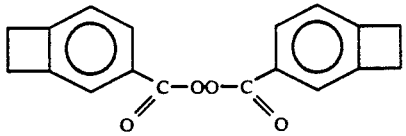

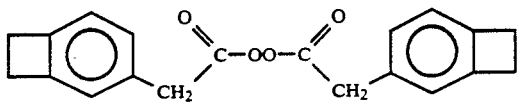

6. The cyclobutarene peroxide of claim 1 represented by the formula:

CBAr—R—OO(—R—R$^2$—OO—)$_n$—X where R and R$^1$ are as previously defined, R$^2$ is hydrocarbylene of 1 to about 20 carbons, n is an integer equal to 1 to about 5 and X is R$_1$ or CBAr.

7. The cyclobutarene peroxide of claim 6 wherein X is CBAr.

8. The cyclobutarene peroxide of claim 7 wherein the cyclobutarene peroxide is represented by any one of the formulae:

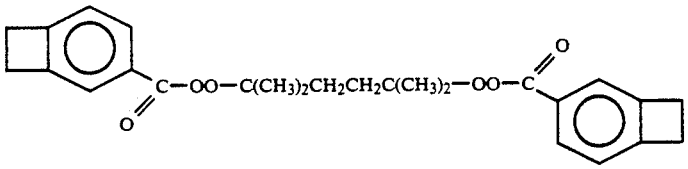

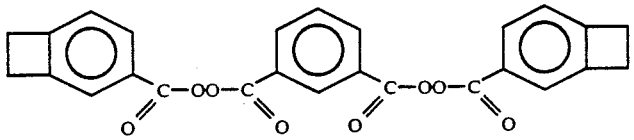

* * * * *